United States Patent [19]

Lissenburg et al.

[11] Patent Number: 4,469,482
[45] Date of Patent: Sep. 4, 1984

[54] DISPOSABLE HYPODERMIC SYRINGE

[75] Inventors: Rokus C. D. Lissenburg, Eindhoven; Paulus R. Kamstra, Olst, both of Netherlands

[73] Assignee: Duphar International Research B.V., Weesp, Netherlands

[21] Appl. No.: 402,077

[22] Filed: Jul. 26, 1982

[30] Foreign Application Priority Data

Jul. 29, 1981 [NL] Netherlands ............... 8103568

[51] Int. Cl.³ .................................... A61M 5/00
[52] U.S. Cl. .................. 604/187; 604/238; 128/765
[58] Field of Search ............. 604/90, 89, 238, 82, 604/218, 220, 191, 187; 128/765; 206/528, 538

[56] References Cited

U.S. PATENT DOCUMENTS

| 2,591,046 | 4/1952 | Brown ............................ 604/90 |
| 3,348,546 | 10/1967 | Roberts et al. ................. 604/90 |
| 3,464,412 | 9/1969 | Schwartz ....................... 604/90 |
| 3,881,484 | 5/1975 | Gidcumb, Jr. ................. 604/89 |
| 4,235,235 | 11/1980 | Bekkering ..................... 604/238 |
| 4,363,329 | 12/1982 | Raitto ........................... 128/765 |

FOREIGN PATENT DOCUMENTS 871854  10/1959  United Kingdom .

Primary Examiner—John D. Yasko
Attorney, Agent, or Firm—Stevens, Davis, Miller & Mosher

[57] ABSTRACT

The invention relates to a disposable syringe comprising a barrel in which a piston is provided and to which a needle is or can be connected to the front, a stopper being present in the barrel between piston and needle or needle connection means. The inner wall of the barrel is locally deformed between stopper and needle or needle connection so that at the area of the deformation injection liquid can reach the cannula past the stopper and during nurse-aspiration the stopper is held, in which body fluid can reach the part of the barrel present behind the stopper.

10 Claims, 5 Drawing Figures

DISPOSABLE HYPODERMIC SYRINGE

The present invention relates to a disposable hypodermic syringe, and in particular to a syringe comprising a barrel which is open at each end and which for the greater part has an inside diameter which remains the same in the longitudinal direction and is rotationally symmetrical, a piston which can be moved in the barrel and seals same, to which piston a piston rod is or can be connected, a needle or means to connect same to the front of the barrel, a stopper the dimenstions of which are such that it can be provided in a sealing manner and be movable between the piston and the needle or needle connection means, and a finger grip or means to connect same to the outside of the barrel.

Such a syringe is known from Netherlands Patent Application No. 7714308 in the name of applicants. When said syringe is used, the injection liquid can pass the stopper through a by-pass recessed in a needle holder. Although the syringe described in this Application has proved to give good satisfaction in practice, it nevertheless has a disadvantage. Prior to administering an injection, it is normally necessary to find out whether the tip of the injection needle is present in the correct place in the patient's body, that is to say whether or not in a blood vessel. Therefore, the piston is usually slightly retracted by means of the piston rod, in which body liquid or no body liquid, respectively, reaches the barrel via the cannula. This process comprises the so-called nurse-aspiration. Because the barrel is manufactured from transparent material, the nurse can see whether the tip of the injection needle is present in a vein, if so desired, and hence whether the injection liquid will be injected directly in the blood circulation system. During said aspiration, the stopper may not be retracted with the piston because as a result of this the by-pass to the barrel might be blocked so that body fluid could not reach the barrel. In this connection it is to be considered that during aspiration the forces which must hold the stopper at the area of the by-pass must be capable of withstanding a considerable pressure on the stopper; in fact, a difference in pressure of approximately 100 kPa can occur on each side of the stopper. In the construction of the syringe known from the above-mentioned Netherlands Patent Application it is not excluded that the stopper during aspiration is slightly retracted, as a result of which the drawing-in of body fluid is prevented.

It is the object of the invention to provide a syringe which on the one hand presents the advantages of the syringe known from the above-mentioned Netherlands Patent Application, namely little residual liquid after use, low resistance to the flow of liquid during the injection, and a comparatively thick closure towards the injection needle to avoid diffusion, but which on the other hand does not exhibit the above-mentioned disadvantage. This object can be achieved with a syringe of the kind mentioned in the opening paragraph which, according to the invention, is characterized in that the inner wall of the barrel between the stopper and the needle or the needle connection means is locally deformed over a length which is slightly larger than the length of the stopper in such manner that the distance between diametrically oppositely located inner wall parts at the area of the deformation varies between a slightly smaller diameter and an at least equally large diameter as the inside diameter of the remaining part of the barrel, so that both upon administering an injection, injection liquid present in the barrel can reach the cannula past the stopper, and during nurse-aspiration the stopper is held at the area of the deformation, in which body fluid can reach the part of the barrel present behind the stopper past the stopper.

Thus the syringe according to the invention offers the certainty that the nurse-aspiration will not be impeded or prevented. This certainty can also be reached with an injection syringe having a needle holder, provided shape and dimensions of the needle holder are such that the stopper during aspiration is held in the needle holder. Therefore, the invention also relates to a syringe comprising a barrel which is open at each end and has a rotationally symmetrical inside diameter which remains the same in the longitudinal direction; a piston which is movable in the barrel and seals same and to which a piston rod is or can be connected; a stopper the dimensions of which are such that is can be provided in a sealing manner in the opening in the front end of the barrel; a finger grip or means to connect same to the outside of the barrel; a needle holder, consisting of a collar provided or to be provided in a sealing manner to the front end of the barrel; a neck in which an injection needle is or can be connected; and a hollow shaft between collar and neck, in which a passage is formed in the inner wall of the shaft and the rear face of the neck, through which passage injection liquid present in the barrel can reach the cannula when the stopper during use of the syringe is moved into the shaft of the needle holder. This syringe is characterized in that the inner wall of the shaft of the needle holder has such a cross-section that the distance between diametrically oppositely located parts of the inner wall of the shaft varies between a slightly smaller diameter and an at least equally large diameter as the inside diameter of the barrel, so that during nurse-aspiration the stopper is held in the shaft and body fluid can reach the barrel past the stopper.

The first-mentioned syringe in which the by-pass for the injection liquid is provided in the wall of the barrel is to be preferred. As a matter of fact, the use of a separate needle holder as in the last-mentioned syringe has the disadvantage that during assembly an extra operation has to be carried out so that the cost-price of the syringe is increased. Moreover, any extra component for a syringe, for example a needle holder, increases the cost-price, of course. On the other hand, the use of a separate needle holder also has a few advantages. As will be explained hereinafter, in a syringe having a needle holder there is the possibility to supply the syringe in a bipartite construction. Another advantage relates to the relatively small tolerance which is permitted in the dimensions of the inner wall of the barrel at the area of the deformation or the inner wall of the shaft of the needle holder, respectively. A plastic component to be manufactured by injection moulding in a mould, for example a needle holder, can be manufactured with very great accuracy; when a barrel wall, generally made of glass, is locally deformed, less accuracy in the dimensions of the deformation will usually be reached.

A syringe having a by-pass in the glass barrel wall is known from literature.

U.S Pat. No. 2,717,601 relates to a barrel for a two-compartment syringe, said barrel comprising a liquid compartment closed by means of a piston and a stopper. By exerting pressure on the piston, the stopper is moved in the direction of a second compartment which comprises a medicament in the solid state. The stopper passes a by-pass which may be formed by grooves recessed in the inner wall or in that the wall is locally compressed to an oval shape. The liquid can reach the second compartment through the by-pass formed so as to be able to dissolve the solid medicament location. After shaking the barrel to dissolve the medicament in the liquid, the resulting injection liquid can be injected in the usual manner.

U.S Pat. No. 3,330,282 relates to a combination of a syringe and a mixing vial; this combination may also be considered to be a two-compartment syringe. The syringe described in said patent also comprises a by-pass in the form of a groove recessed in the inner wall past which the liquid can pass the stopper so as to be able to reach the solid medicament in the mixing vial in this manner. In order to prevent the stopper from blocking the entrance to the cannula at the area of the by-pass, the stopper has two projections which keep the stopper at some distance from said entrance.

A two-compartment syringe is also described in the British Patent Specification No. 871,854. This known injection syringe has two compartments separated by a stopper, the forward compartment comprising a solid medicament, the rearward one comprising the solvent for this medicament. The solid medicament is sealingly closed up between said stopper and a sealing member, the solvent between said stopper and a piston. By retracting the piston and the stopper, rigidly connected with the piston by a piston rod, the pressure in the medicament compartment is reduced, as a result of which the solvent flows in this compartment. A by-pass in the stopper enables the solvent to pass the stopper, this by-pass is formed by wedge-shaped projections on the inner wall of the syringe ampoule.

The by-pass construction in the syringe according to the present invention is meant for a pre-filled single-compartment syringe and not for a multi-compartment syringe. Therefore, other requirements are imposed upon the shape and construction of the syringe according to the invention than upon those of the above-mentioned known syringes. The necessity of being able, during nurse-aspiration, to fix the stopper at the area of the by-pass is not present in the two-compartment syringes described in the above-mentioned U.S. patents. In fact, in such two-compartment syringes aspiration is necessary only when the solid medicament has dissolved in the solvent, so when stopper and piston engage each other. During aspiration, piston and stopper are retracted together, so that aspiration can take place in an unimpeded manner.

The local deformation of the inner wall of the barrel or the narrowing in the shaft of the needle holder of the syringe according to the invention may be made in various manners. Preferably, the inner wall of the barrel at the area of the deformation or the inner wall of the shaft of the needle holder has one or more ridges which extend in the longitudinal direction of the barrel and shaft, respectively. Such a ridge or ridges can very easily be provided; in addition, the dimensions of the ridge or ridges can accurately be determined so that exactly the desired holding forces can be reached which have to act on the stopper at the area of the ridge or ridges.

In another embodiment, the inner wall of the barrel at the area of the deformation or the inner wall of the shaft of the needle holder has an oval cross-section. In that case the inner wall of the barrel at the area of the deformation or the inner wall of the shaft and the rear face of the neck of the needle holder may also comprise one or more slots, so that during use of the syringe the cannula is better accessible for the injection liquid.

The wall of a glass barrel can be locally deformed by locally heating the glass and depressing it, blowing it out or compressing it to an oval shape with the aid of the known techniques available for this purpose. The plastic needle holder is manufactured in the correct shape by injection moulding by means of a suitable mould.

In order to be able to expel the injection liquid as completely as possible, in other words, in order to have left as little injection liquid as possible in the syringe after the use of the syringe, it is very much desirable that towards the end of the injection, when the front side of the piston has contacted the rear side of the stopper, the stopper is pushed forward by means of the piston. This is achieved by causing the holding forces which act on the stopper at the area of the deformation of the inner wall of the barrel or which act on the stopper in the shaft of the needle holder, to be smaller than the force which is exerted on the piston during normal use of the syringe.

It will be obvious that the invention also relates to a pre-filled syringe, that is to say a syringe filled with injection liquid.

In the construction having a needle holder, the syringe according to the invention is particularly suitable for a bipartite construction. In that case the first part is formed by the barrel with injection liquid in which the stopper and the piston are provided, and which, if desired, has a finger grip and/or a piston rod. The second part of the syringe is formed by the needle holder having an injection needle connected thereto, if so desired. This two-part construction has the advantages indicated in the above-mentioned Netherlands Patent Application No. 7714308. For example, it is possible to provide the user individually with a needle holder with needles of different dimensions, so that he or she can choose the correct needle for each individual case. The barrel with medicament which is also supplied separately is the only part of the syringe which is restricted to an expiration term and/or is to be subjected to a special treatment, for example, post-sterilization, storage in the dark and/or under cooling. This not only has advantages from a point of view of technical production but is also of importance for a more economic production method.

BRIEF DESCRIPTION OF THE DRAWINGS

The invention will now be described in greater detail with reference to preferred embodiments which are shown in the drawing, in which.

DESCRIPTION OF THE PREFERRED EMBODIMENTS

Figure 1:
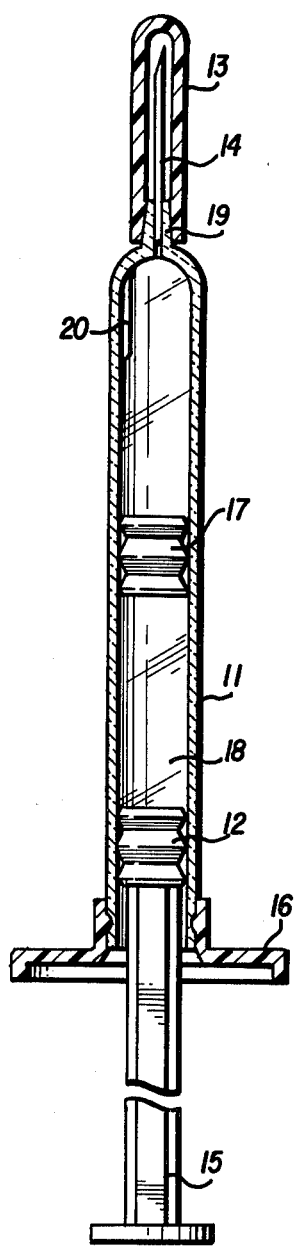
FIG. 1 is a longitudinal sectional view of a syringe according to the invention in the condition in which it can be transported and stored.
Figure 2:
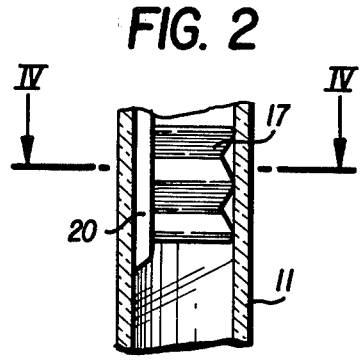
FIG. 2 shows an essential part of the syringe of FIG. 1, but now in the condition in which it is ready for administrating an injection.
Figure 4:
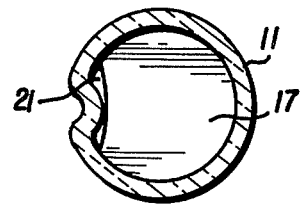
FIG. 4 is a cross-sectional view through the barrel of the syringe according to the preceding Figures, namely along the line IV—IV in FIG. 2.

The embodiment of the syringe according to the invention shown in FIGS. 1, 2 and 4 has proved to be particularly suitable.

The syringe shown in FIG. 1 comprises a barrel 11, in which a piston 12 is provided at one end while the other end has an injection needle 14 surrounded by a needle guard 13.

The piston can be moved by means of a piston rod 15 which can be connected to the piston, for example, by means of a screwing operation. At the same end where the piston is present, the barrel has a finger grip 16 connected around the barrel according to the so-called snap-cap principle. Another likewise reliable connection of a finger grip is described in British Patent Specification No. 1479536 in the name of applicants; the finger grip described in this Specification consists of a tensioning collet which is clamped around the end of the barrel by means of a tensioning sleeve. The finger grip preferably is of slightly resilient material for example, plastic. The barrel is manufactured from rigid material, for example, glass. In another embodiment the finger grip is a radially projecting flange-like part of the barrel. Of course, other constructions known to those skilled in the art are possible.

A stopper 17 closing the barrel is present in the part of the barrel remote from the piston. The stopper and the piston, are manufactured from resilient material, preferably from rubber of a pharmaceutical quality. An injection liquid 18 is present in the barrel between the piston and the stopper.

The injection needle 14 may be connected to the barrel 11 by means of a needle connection means, for example, a needle holder as described in Netherlands Patent Application No. 7603511 in the name of Applicants. This needle holder, usually manufactured from deformation-proof, rigid plastic material, keeps the needle clamped and is connected to the end of the barrel, for example, by means of a snap-cap construction. In another embodiment, the needle holder may be connected to the barrel by means of a screw or bayonet joint, or, when the barrel also has a connection edge or connection collar, by means of riveting or shrinking. In again another embodiment, as shown in FIG. 1, the barrel is narrowed at the area of the needle connection, so that the needle 14 can be connected in the formed mouth or spout 19, for example, by means of a suitable glue or lute. The injection needle has a needle guard 13 which keeps the needle sterile during storage and transport.

Figure 3:
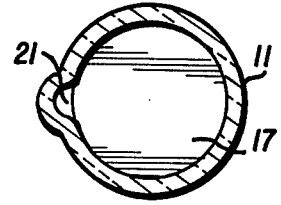
FIGS. 3 and 5 are cross-sectional views through the barrel of a syringe taken along the same line as indicated in FIG. 2, but this time of other embodiments of the syringe according to the invention.
Figure 5:
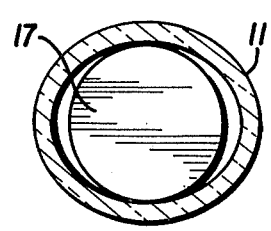

The inner wall of the barrel is locally deformed. This deformation may be a ridge 20 which extends in the longitudinal direction of the barrel. This is better visible in FIG. 4 which is a cross-sectional view through the barrel of the syringe taken on the line IV—IV of FIG. 2. The ridge 20 is slightly longer than the stopper 17 and may be formed on the inner wall of the barrel by locally heating the glass wall of the barrel and depressing it. In another embodiment the inner wall of the barrel may be deformed by locally heating the wall of the barrel and compressing it to an oval shape. As shown in FIG. 5, both the inner wall and the outer wall of the barrel obtain an oval cross-section at the area of the deformation. This oval deformation of the barrel should also be slightly longer than the length of the stopper. In still another embodiment which is shown in outline in FIG. 3, the barrel has, in addition to the oval deformation, a slot or channel 21 which extends in the longitudinal direction of the barrel and which is slightly longer than the stopper and through which the injection liquid can pass the stopper even more easily.

When using the syringe according to the invention, the piston 12 is moved forward by means of the piston rod 15. The pressure exerted on the piston propagates to the stopper 17 via the fluid column 18. When the stopper has reached the position shown in FIG. 2, the stopper is clamped by the ridge 20. As a result of the deformation of the flexible material of the stopper, small ducts are formed on either side of the ridge, as is clearly shown in FIG. 4. At this instant the user can find out whether the tip of the injection needle is in the correct place in the patient's body, by aspirating. During said nurse-aspiration, the stopper remains fixed at the area, so that body fluid can enter the barrel through the ducts. The actual injection is then administered, in which the injection liquid can pass the stopper via the ducts and can thus reach the cannula. In the embodiments shown in FIGS. 3 and 5 the injection liquid at the area of the widening of the barrel wall can pass the stopper. When the injection liquid between stopper and piston has been expelled as completely as possible, and hence has been injected into the patient, the front of the piston contacts the rear side of the stopper. It will be obvious that the front of the piston and the rear of the stopper are substantially complementary and are substantially preferably flat faces, to keep the residual volume of injection liquid as small as possible. The stopper is now pushed forward further by the piston out of the position in which the stopper was held due to the deformation of the barrel, after which the injection liquid present between stopper and cannula is expelled as completely as possible. The front of the stopper is preferably shaped so that in the foremost position the room between the front of the stopper and the rear of the mouth or spout 19 is as small as possible.

In another embodiment the invention syringe does not have a needle in the position in which the syringe is stored, but has a needle connection means. When such a syringe is used, the needle, after the protective cap has been removed, is put on a needle holder by means of a needle cone, for example, a so-called Luer cone. In this embodiment the aperture in the neck of the needle holder is closed on the outside by means of a protective cap which ensures the sterility of that part of the needle holder and hence of the interior of the syringe.

We claim:

1. A syringe comprising a barrel which is open at each end and which for the greater part has an inside diameter which remains the same in the longitudinal direction and is rotationally symmetrical; a piston which can be moved in the barrel and seals same, to which piston a piston rod is or can be connected; a needle or means to connect same to the front of the barrel; a stopper, the dimensions of which are such that it can be provided in a sealing manner and be movable between the piston and the needle or needle connection means; and a finger grip or means to connect same to the outside of the barrel, said syringe being characterized in that the inner wall of the barrel is locally deformed from the front of the barrel toward the stopper over a length which is slightly greater than the length of the stopper and in a manner such that the distance between diametrically oppositely located inner wall parts at the area of the deformation varies between a slightly smaller diameter and an at least equally large diameter as the inside diameter of the remaining part of the barrel, so that upon administering an injection, injection liquid present in the barrel can reach the cannula by flowing past the stopper, and during nurse-aspiration the stopper is held at the area of the deformation, thereby allowing body fluid to reach the part of the barrel present behind the stopper by flowing past the stopper.

2. A syringe comprising a barrel which is open at each end and has a rotationally symmetrical inside diameter which remains the same in the longitudinal direction; a piston which is movable in the barrel and seals same and to which a piston rod is or can be connected; a stopper, the dimensions of which are such that it can be provided in a sealing manner in the opening in the front of the barrel; a finger grip or means to connect same to the outside of the barrel; and a needle holder comprising a collar adapted to be connected in a sealing manner to the front of the barrel, a neck in which an injection needle is or can be connected, and a hollow shaft between the collar and the neck, said needle holder including a passage formed in the inner wall of the shaft and the rear face of the neck through which injection liquid present in the barrel can reach the cannula when the stopper during use of the syringe is moved into the shaft of the needle holder, said syringe being characterized in that the inner wall of the shaft of the needle holder has a cross-section such that the distance between diametrically oppositely located parts of the inner wall of the shaft varies between a slightly smaller diameter and an at least equally large diameter as the inside diameter of the barrel, so that during nurse-aspiration the stopper is held in the shaft and body fluid can reach the part of the barrel present behind the stopper by flowing past the stopper.

3. A syringe as claimed in claim 1 or 2, characterized in that the inner wall of the barrel at the area of the deformation or the inner wall of the shaft of the needle holder comprises one or more ridges which extend in the longitudinal direction of the barrel or the shaft, respectively.

4. A syringe as claimed in claim 5, 1 or 2, characterized in that the inner wall of the barrel at the area of the deformation or the inner wall of the shaft of the needle holder has an oval cross-section.

5. A syringe as claimed in claim 4, characterized in that the inner wall of the barrel at the area of the deformation or the inner wall of the shaft and the rear face of the needle holder comprise one or more slots through which during use of the syringe the injection liquid can reach the cannula.

6. A syringe as claimed in Claims 1 or 2, characterized in that the holding forces which act on the stopper at the area of the deformation of the inner wall of the barrel or which act on the stopper in the shaft of the needle holder, are smaller than the force which is exerted on the piston during the injection, so that towards the end of the injection the piston can push the stopper forward, thereby allowing the injection liquid present between the stopper and the cannula to be expelled as completely as possible.

7. A syringe as claimed in Claims 1 or 2, characterized in that the barrel is filled with an injection liquid which is enclosed between the piston and the stopper present in the barrel.

8. A barrel for a syringe comprising a barrel that is open at each end and for the greater part has an inside diameter which remains the same in the longitudinal direction and which is rotationally symmetrical; a piston which is movable in the barrel and seals same; and a stopper which can also be moved in the barrel and seals same, characterized in that the inner wall of the barrel is locally deformed from an end of the barrel remote from the piston toward the piston over a length which is slightly greater than the length of the stopper and in a manner such that the distance between diametrically oppositely located inner wall parts at the area of the deformation varies between a slightly smaller diameter and an at least equally large diameter as the inside diameter of the remaining part of the barrel.

9. A needle holder for a syringe as claimed in claim 2, comprising a collar with which the needle holder can be connected to the front of the barrel in a sealing manner, a neck in which an injection needle can be provided, and a hollow shaft connecting the collar to the neck in a sealing manner, characterized in that the shaft has such a cross-section that the distance between diametrically oppositely located inner wall parts varies between a slightly smaller diameter and an at least equally large diameter as the inside diameter of the barrel to be connected to the needle holder.

10. A syringe as claimed in Claim 1, characterized in that it comprises a needle holder optionally provided with an injection needle, and a separate barrel to be connected to the needle holder, which barrel has a piston to which a piston rod is or can be connected, a stopper, and a finger grip or means for the connection thereof.

* * * * *